United States Patent [19]

Bernardi et al.

[11] Patent Number: 5,225,530
[45] Date of Patent: Jul. 6, 1993

[54] POLYPEPTIDE USEFUL FOR THE PREPARATION OF ANTIMALARIAL VACCINES AND OF DIAGNOSTIC KITS FOR THE DETECTION OF MALARIAL AFFECTIONS

[75] Inventors: Adriano Bernardi, Monterotondo; Fabio Bonelli; Antonello Pessi, both of Rome; Antonio S. Verdini, Monterotondo, all of Italy

[73] Assignee: Eniricerche S.p.A., Milan, Italy

[21] Appl. No.: 803,483

[22] Filed: Dec. 4, 1991

Related U.S. Application Data

[63] Continuation of Ser. No. 68,121, Jun. 29, 1987, abandoned.

[30] Foreign Application Priority Data

Jul. 16, 1986 [IT] Italy ............................ 21144 A/86

[51] Int. Cl.$^5$ .............................................. C07K 7/10
[52] U.S. Cl. ..................................... 530/324; 424/88; 530/325; 530/326
[58] Field of Search ................ 424/88; 530/326, 325, 530/324

[56] References Cited

U.S. PATENT DOCUMENTS 4,693,994 9/1987 McCutchan et al. ................. 514/15
4,707,357 11/1987 Dame et al. ............................ 424/88
4,886,782 12/1989 Good et al. ............................ 514/12
4,997,647 3/1991 Nussenzweig et al. ................ 424/88

FOREIGN PATENT DOCUMENTS 0166410 1/1986 European Pat. Off. ............ 530/324
0209643 1/1987 European Pat. Off. .
8605790 10/1986 PCT Int'l Appl. .

OTHER PUBLICATIONS

Stewart and Young, *Solid Phase Peptide Synthesis*, 2nd ed., Pierce Chemical Co., 1984, pp. 1–18, 99–103.
Zavala, et al., *Science*, 228:1436, 1985.
Perspectives in Peptide Chemistry, pp. 101–117 (Karger, Bosel 1981).
JACS Chem. Comm., 1978, pp. 537–539.

*Primary Examiner*—Lester L. Lee
*Attorney, Agent, or Firm*—Hedman, Gibson & Costigan

[57] ABSTRACT

Polypeptide useful for the preparation of antimalarial vaccines and of diagnostic kits for the detection of antisporozoite antibodies in clinical samples of malariated persons, constituted by: a synthetic peptide, which repeates the region I of *P. falciparum* and by a variable number of repetitive tetrapeptide units of CS protein of *P. falciparum* linked to each other by an amidic bond between the tail proline of I region and the head asparagine of the first tetrapeptide.

2 Claims, 3 Drawing Sheets

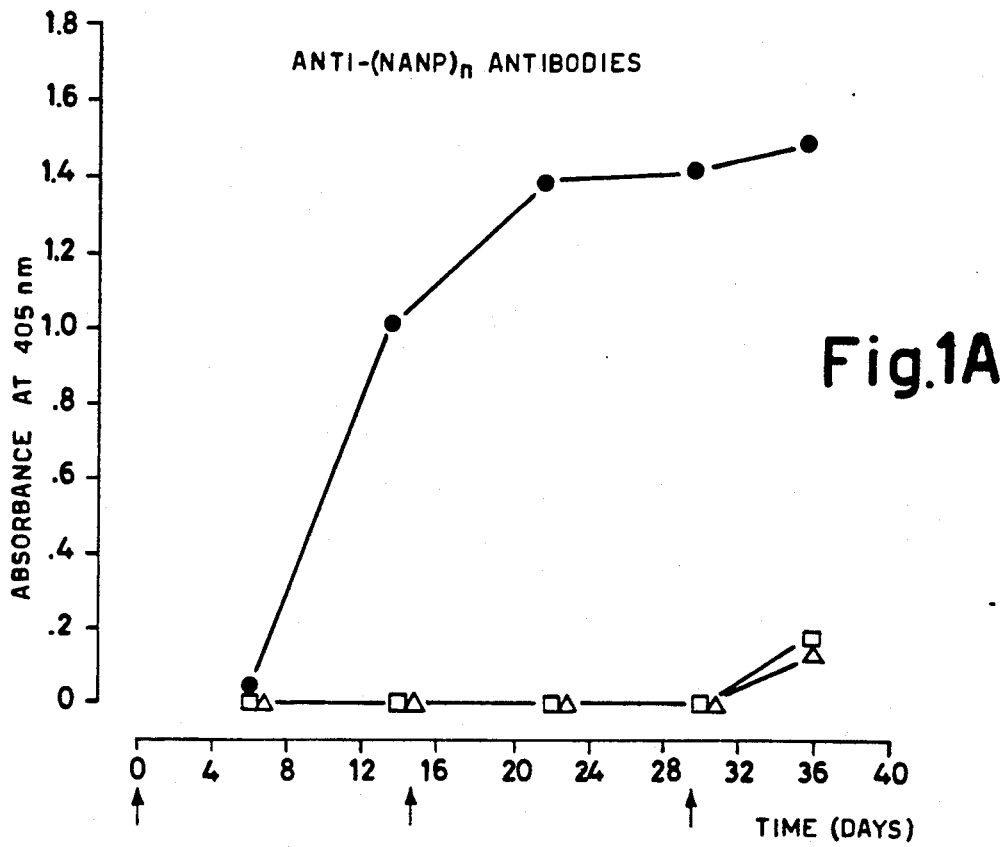
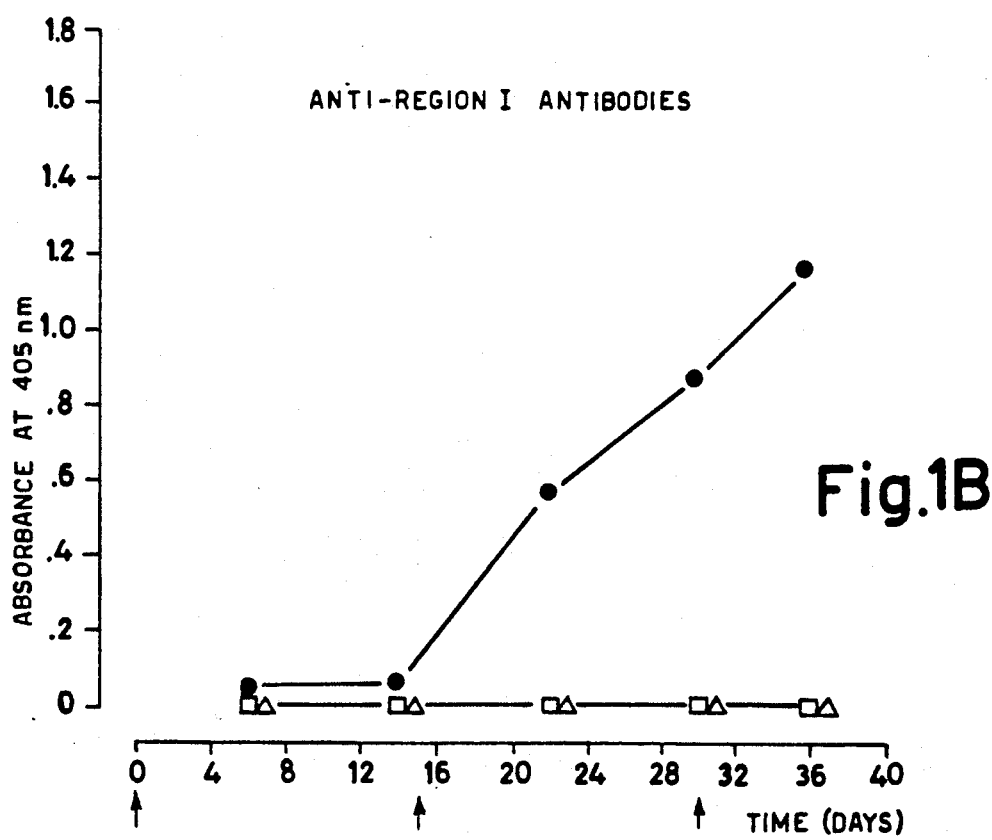

Fig.3
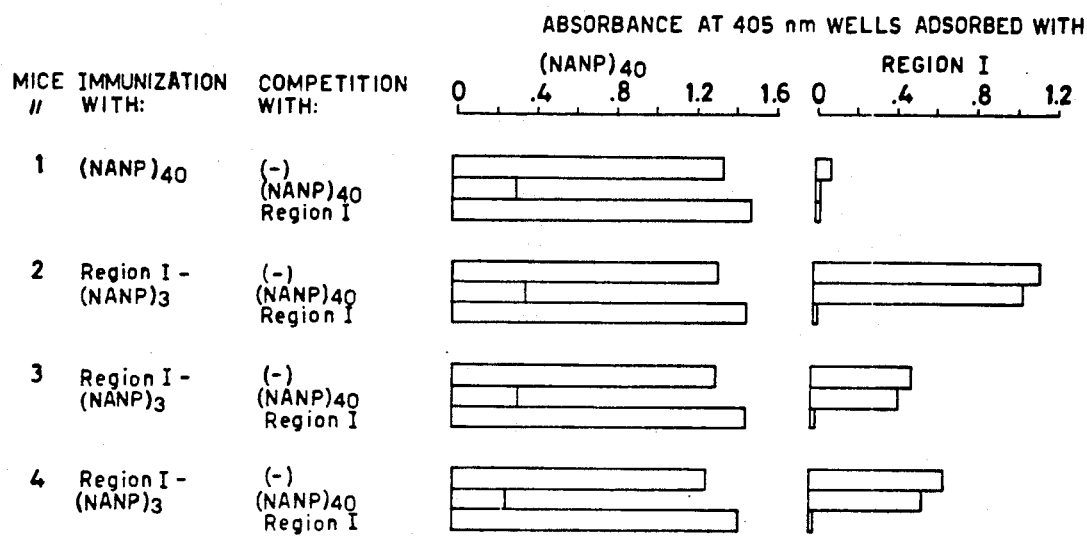
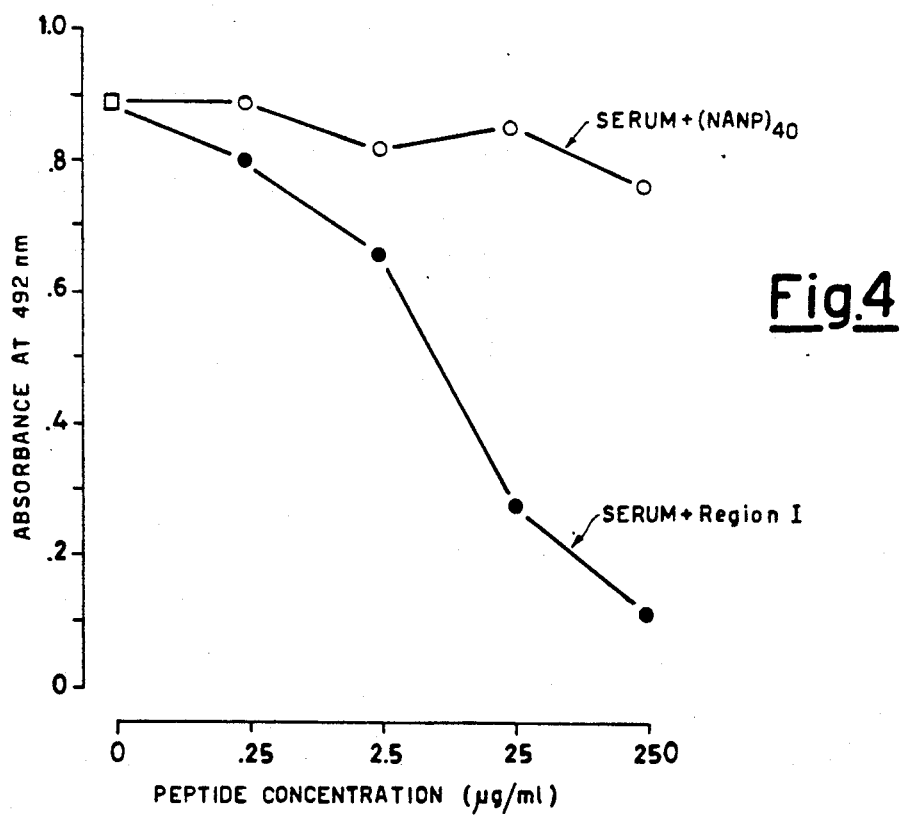
Fig.4

POLYPEPTIDE USEFUL FOR THE PREPARATION OF ANTIMALARIAL VACCINES AND OF DIAGNOSTIC KITS FOR THE DETECTION OF MALARIAL AFFECTIONS

This is a continuation of application Ser. No. 07/068,121, filed Jun. 29, 1987, and now abandoned.

The present invention relates to a polypeptide useful for the preparation of antimalarial vaccines and of diagnostic kits for the detection of antisporozoite antibodies in clinical samples from malariated persons.

The etiologic agent of the disease is a protozoan belonging to Plasmodium genus, having a vital cycle alternating between an invertebrate host, wherein it shows a sexual form of reproduction, and a vertebrate host, inside which it multiplies by schizogenesis.

Among the many species of Plasmodium which cause malaria in vertebrate hosts, only four are pathogen for man: *Plasmodium ovalis, Plasmodium malariae, Plasmodium vivax, Plasmodium falciparum*.

This latter, in particular, is the ethiologic agent in the most serious form of malaria, the so-said malignant tertian malaria.

Notwithstanding the development of new insecticides and drugs, such as chloroquine, malaria is presently among the most serious parasitic diseases.

Said disease is estimated in fact to strike, each year, from 200 to 400 million people, causing a mortality rate during the early infancy which can be as high as 50% of cases.

The more and more pressing need derives from what above said, for developing an efficacious antimalarial vaccine, i.e., a vaccine which is capable of stimulating the immunitary system to produce antibodies which are able to attack and neutralize the parasite, and develop a long-term protective immunity, not depending on Plasmodium species.

However, the complexity of the vital cycle of the parasite, characterized by many potential targets for the action of specific immunological processes did not make it heretofore possible a vaccine endowed with the desired characteristics to be developed.

The malarial infection in man begins with the anopheles mosquito bite, which releases, inside the blood stream, a certain number of sporozoites.

Within one hour, each sporozoite reaches a hepatic cell wherein it, after undergoing a complex series of transformations, gives rise to the formation of merozoites.

Then, each merozoite invades an erythrocyte, wherein it multiplies asexually, until the herithrocyte explodes and releases from 10 to 20 new merozoites.

Some of these develop male and female gametocytes, thus starting the sexual cycle of the parasite.

The gametocytes are then sucked by a mosquito, together with the herythrocytes, come to maturity inside its digestive tube, and merge forming a zygote.

This latter undergoes eventually a series of divisions and transformations, which lead to the formation of a mature sporozoite, ready to start a new infective cycle.

Therefore, a protective immunity can act both against the sporozoites, and against the asexual blood forms of the parasite.

Particularly interesting is the development of a vaccine against the sporozoites of the parasite which, if efficacious on man, can prevent the following stages to develop, which are responsible for the disease and for the transmission of the infection.

The main surface antigen of the sporozoite of *P. Berghei* (R. S. Nussenzweig et al., Science 207, 71, 1980) and of Plasmodium, which cause malaria in monkeys and in man (F. Santoro et al., J. Biol. Chem. 258, 3341, 1983; E. H. Nardin et al., J. Exp. Med. 156, 20, 1982) is a membrane protein, which coats the whole surface of the sporozoite; it is said "circumsporozoitic protein" or "CS protein".

Dame et al. have recently disclosed, in EP 166,410 Patent application, the cloning of the gene codifying for CS protein of *P. falciparum*, whose sequence is characterized by a central domain formed by 37 tetrapeptides with an (Asn-Ala-Asn-Pro) (NANP) sequence and 4 tetrapeptides (Asn-Val-Asp-Pro), flanked by shorter aminoacidic sequences respectively denominated as "Region I" ("RI") and "Region II" ("RII").

By using monoclonal antibodies, Dame et al. found that the immunodominant epitope of said protein is constituted by the repeating sequence, and synthetized peptides containing from 1 to 3 (NANP) tetrapeptides capable of blocking the bond of monoclonal antibodies to CS protein.

To date, other five surface proteins (CS proteins) of Plasmodium have been identified, and they all show the same character of repetitivity of the aminoacidic sequences and immunogenicity. Thus, synthetic peptides containing, or constituted by, said repetitive sequences, appear to be particularly suitable for the preparation of an antimalarial vaccine.

It was observed however that, whilst the aminoacidic sequence is maintained inside the repeating peptide, said sequence can vary between species and, in some cases, inside the same species (S. Sharna et al., Science 229, 779, 51985).

This constitutes a limitation in the immunoprophylaxis of malaria, in that a vaccine based on use of species-specific immunogens shows a limited efficacy.

Dame et al (EP 166,410) and L. S. Ozaki et al. (Cell 34, 815, 1985) have observed that the Region I, which flanks the central domain of CS protein shows, differently from the repeating epitope, a considerable sequential analogy inside different Plasmodium species and shows a high polarity. It could be inferred hence that such region can be involved in determined functions of the sporozoite, and constitute hence a suitable immunogen for the preparation of an antimalarial vaccine.

The immunogenicity of CS Region I of *P. falciparum* was then determined by injecting said region into test animals, in the form of a synthetic peptide conjugated with a heterologous proteinic support (Ballou et al., Science 228 953, 1985; U. Vergara et al., J. Immunol. 134, 3445 (1985).

It was found thus that said peptides induce the formation of antibodies capable of recognizing the sporozoites of different species of Plasmodium, but are incapable of preventing the penetration of human hepatic cells by the sporozoites, of causing a reaction of CS protein precipitation (Ballou et al.), and of stimulating the proliferation of T lymphocytes (V. Vergara et al.), essential for generating an immunity memory.

Said synthetic peptides appear hence to be not much suitable for the development of an antimalarial vaccine, in that they are not able to give an in vivo protection (Ballou et al.), or to induce a long-term immunity.

We found now that it is possible to overcome the drawbacks of the prior art, by means of a polypeptide constituted by the synthetic peptide of Region I bonded by means of a covalent bond to a homologous proteinic carrier, which can be obtained in a pure form by means of a simple and economically favourable process.

A purpose of the present invention is therefore a polypeptide useful for the preparation of antimalarial vaccines and of diagnostic kits for detecting antisporozoite antibodies in clinical samples withdrawn from malariated persons.

Another purpose of the present invention is a process for the preparation of said polypeptide.

Still another purpose of the present invention is the use of said polypeptide for preparing antimalarial vaccines and diagnostic kits for detecting antisporozoite antibodies in clinical samples withdrawn from malariated persons.

Still further purposes of the invention will be clear from the following disclosure of the text and from the hereto attached drawings.

The polypeptide according to the present invention is constituted by the synthetic peptide which repeats the Region I of *P. falciparum* and by a variable number of units of the repeating tetrapeptide (NANP) of CS protein of *P. falciparum*, linked with each other by an amidic bond between the tail proline of Region I and the head asparagine of the first polypeptide.

In particular, the polypeptide of the present invention can be defined by means of the following general formula:

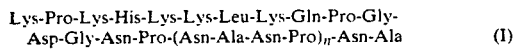

Lys-Pro-Lys-His-Lys-Lys-Leu-Lys-Gln-Pro-Gly-
    Asp-Gly-Asn-Pro-(Asn-Ala-Asn-Pro)$_n$-Asn-Ala   (I)

wherein:
Asn = asparagine
Ala = alanine
Asp = aspartic acid
Lys = lysine
Leu = leucine
His = Histidine
Gly = glycine
Gln = glutamic acid
Pro = proline
and n has a value comprised within the range of from 3 to 40.

The polypeptide (I) can be prepared, according to known general techniques, either in homogeneous phase, or in solid phase.

According to the present invention, the polypeptide (I) is synthetized in the solid phase by means of a process comprising:

a) the condensation of the first aminoacid protected on the α-amino group onto an insoluble solid support by means of a reaction of esterification between the activated carboxy group and the connection hook of the solid support;

b) the removal of the protecting group from the α-amino group;

c) the condensation of the aminoacid bonded to the insoluble solid support to a second aminoacid protected on its α-amino group by means of a reaction of acylation between the de-protected amino group and the activated carboxy group of the second aminoacid;

d) the removal of the α-amino-protecting group from the second aminoacid;

e) the condensation of the successive aminoacids according to the strategies as per above (c) and (d) steps, until polypeptide (I) is complete;

f) the removal of the so-obtained polypeptide (I) from the insoluble solid support by means of an acidic hydrolysis;

g) the recovery and purification of polypeptide (I) by chromatography.

According to the present invention, insoluble solid supports are selected from polyacrylamidic resins, polystyrene resins crosslinked with divinyl-benzene, phenolic resins.

In particular, a commercial polyacrylamidic resin is used, which is functionalized with norleucine (Nle) as the internal reference aminoacid, and a hook for the reversible peptide-resin connection, such as, e.g., p-hydroxymethylphenoxyacetic acid.

Before condensing the aminoacids, the functionalized resin is swollen by being treated with N,N-dimethylformamide (DMF), at room temperature, or at temperatures close to room temperature.

According to the present invention, the aminoacids can be added to the resin either individually or, after a preliminary synthesis in homogeneous phase, as preconstituted peptides. The aminoacids are condensed onto the resin after a preliminary protection of the α-amino group, and of the possible branched reactive functions, and the activation of the end carboxy group.

Examples of α-amino protecting groups suitable for the intended purpose are: benzyloxycarbonyl, triphenylmethyl, tert.amyloxycarbonyl, 2-nitrophenylsulphonyl, fluorenylmethyloxycarbonyl (Fmoc) and tert.butyloxycarbonyl (Boc).

From these, Fmoc and Boc groups, which can be removed under mild conditions, are preferred.

The fluorenylmethyloxycarbonyl (Fmoc) group is particularly preferred.

Possible reactive functional groups present in the side chains of the aminoacids are protected with protecting groups known the art of peptide syntheses.

Typically, protecting groups are used, which are stable under the conditions of removal of the α-amino protecting group.

Examples of said protecting groups are: for lysine: tert.butyloxycarbonyl (Boc), ortho-bromobenzyloxycarbonyl (BrZ) or benzyloxycarbonyl; for aspartic acid, tert.butylester (OBu$^t$) and for histidine: triphenylmethyl (Tritil-Trt) group.

Said protecting groups are removed simultaneously with the removal of polypeptide (I) from the resin.

According to the present invention, the activation of the aminoacidic radicals Lys, Leu, Ala, Pro, Asp and Gly is carried out by means of the reaction with dicyclohexylcarbodiimide (DCI), for forming the symmetrical anhydride of said aminoacid at the end carboxy group.

Generally, the reaction is carried out by dissolving the aminoacid, with its α-amino group being protected, in an inert (non-reactive) organic solvent, in the presence of dicyclohexylcarbodiimide, at room temperature (20°-25° C.).

At reaction end, dicyclohexylurea is filtered or centrifuged off, the solvent is evaporated off and the so-formed symmetrical anhydride is recovered.

The activation of Asn and Gln aminoacid radicals is carried out by means of the reaction with a derivative of phenol, to form the active ester on end carboxy group.

Phenol derivatives which can be used in the process of the present invention are the fluorinated or chlorinated phenol derivatives, such as, e.g., pentachlorophenol, trichlorophenol, pentafluorophenol and p-nitrophenol.

The reaction of activation of the carboxy group of the α-amino protected aminoacid is carried out by contacting said aminoacid and said phenol derivative in an inert organic solvent, at room, or nearly room, temperatures.

Examples of organic acids suitable for the intended purpose are selected from the aprotic solvents, such as, e.g., ethyl acetate or aliphatic chlorocarbons.

The so obtained solution is then cooled to a temperature of about 0° C. and to it a condensation agent is added, with a condensation agent/aminoacid molar ratio equal to, or approximately equal to, 1.

The condensation agent typically used is dicyclohexylcarbodiimide (DCI).

THE (A) STEP

In the (A) step of the process of the present invention, the reaction of esterification between the symmetrical anhydride of the α-amino protected Ala aminoacid and the connection hook of the resin is carried out in an inert organic solvent, in the presence of catalysts.

Organic solvents suitable for the intended purpose are selected from aliphatic chlorocarbons, aliphatic ketones or alkyl esters.

Specific examples for said solvents are N,N-dimethylformamide (DMF), chloroform, ethyl acetate, tetrahydrofuran.

The catalysts are selected from those known from the art. In particular, p-dimethylaminopyridine is used.

The temperatures at which the esterification reaction is carried out can generally range from −10° C. to 40°, and the corresponding times are the required times for completing, or substantially completing, the reaction.

THE (B) AND (D) STEP

At the end of the esterification reaction, in the (B) step the protecting group is removed from α-amino group.

In particular, when the protecting group is fluorenylmethyloxycarbonyl (Fmoc), such removal is carried out by treating the peptide-resin with a (20:80, v/v) piperidine/DMF mixture for a total time of approximately 10 minutes.

THE (C) AND (E) STEPS

After the removal of the α-amino protecting group, and suitable peptide-resin washings, in the (C) and (E) steps of the present invention the successive aminoacids are condensed by means of the acylation reaction between the aminoacids, suitably protected and pre-activated in correspondence of their carboxy group, and the deprotected amino group of the aminoacid bonded to the resin.

In particular, the acylating reaction is carried out in an inert organic solvent, in the presence, or not, of catalysts.

The inert organic solvents are selected from aliphatic chlorocarbons, aliphatic ketones or alkyl esters. Preferably, N,N-dimethylformamide (DMF), chloroform, ethyl acetate, tetrahydrofuran are used.

The catalysts are selected from those known from the art.

In particular, for the Asn and Gln radicals, 1-hydroxybenzotriazole (HOBT) is used.

The temperatures at which the acylation reaction is carried out can generally range from −10° to 40° C.

The reaction is preferably carried out at room, or nearly room, temperature, and the corresponding times are those necessary for completing, or substantially completing, the reaction.

THE (F) STEP

The removal of polypeptide (I) from the insoluble solid support can be carried out according to known general techniques by acidic or basic hydrolysis, aminolysis or alcoholysis.

The reaction is typically carried out by suspending the peptide-resin in a (90:10, v/v) trifluoroacetic acid/water solution, at a temperature of from 10° to 30° C.

At reaction end, the resin is filtered off from the reaction mixture, is repeatedly washed with water and is filtered again.

The combined filtrates are concentrated to dryness by evaporation, are dissolved in water and freeze-dried.

THE (G) STEP

The raw polypeptide (I) obtained from (F) step is then purified by the sequence of gel-filtration chromatography and ion-exchange chromatography.

The fractions corresponding to the desired product are collected and freeze-dried.

At the end of the process of the present invention, an overall chromatographic yield of 74%, and a yield of purified fraction of 40% relatively to the resin-released polypeptide is obtained.

Polypeptides of formula (I) are endowed with a good immunogenic activity.

The peptides wherein n ranges from 3 to 10 are particularly suitable for the purposes of the present invention.

According to the present invention, the immunogenicity of polypeptide RI-(NANP)$_3$-NA synthetized as shown in Example 1 was tested by immunizing inbred mice of different species and analysing, by the ELISA and immuno-fluorescence test the sera withdrawn after different time intervals from the inoculi.

The results obtained show that the antibodies formed are Region I-specific, that they recognize the sporozoites of *P. falciparum* and inhibit the penetration of human hepatic cells by the sporozoites to a higher extent than obtained with sera from mice immunized with the repeating peptide (NANP)$_n$ only.

It was furthermore found that polypeptide RI-(NANP)$_3$-NA induces the proliferation of T cells.

The use of said polypeptide in an ELISA test made it possible to detect, in sera of persons exposed to malarial infection, the presence of anti-Region I antibodies both in sera positive for anti-(NANP)$_{40}$ antibodies and in sera which resulted negative for said antibodies.

Therefore, said polypeptides can be used for the preparation of an antimalarial vaccine and of diagnostic kits for detecting antisporozoite antibodies in clinical samples of malariated persons.

BRIEF EXPLANATION OF THE FIGURES

FIGS. 1A and 1B: Antibody response to RI-(NANP)$_3$-NA polypeptide in C57 BL/6 mice (○), BALB/c mice (□) and CBA/ca (Δ) mice immunized by means of said polypetide.

The sera were tested by the ELISA test on microslabs coated with (NANP)$_{40}$, 1 μg/ml (FIG. 1A); or with RI peptide, 10 μg/ml (FIG. 1B).

The arrows show the immunization days.

Figure 2A:
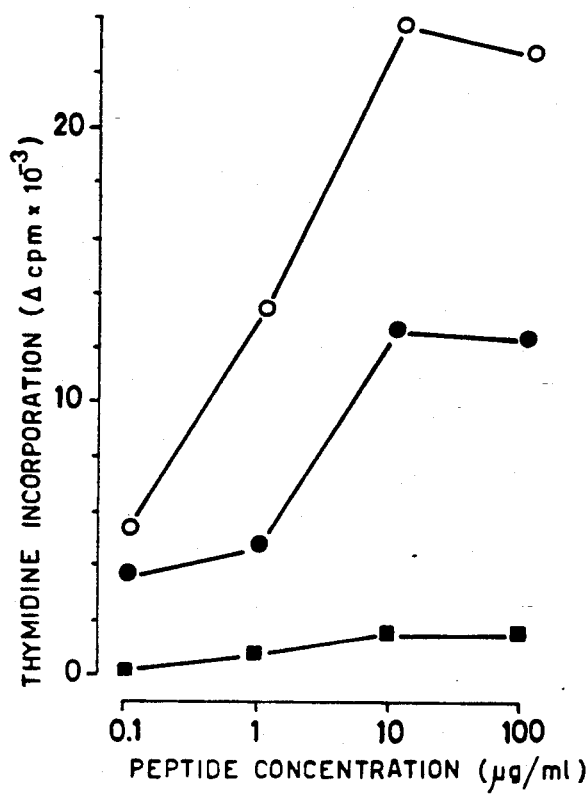
Figure 2B:
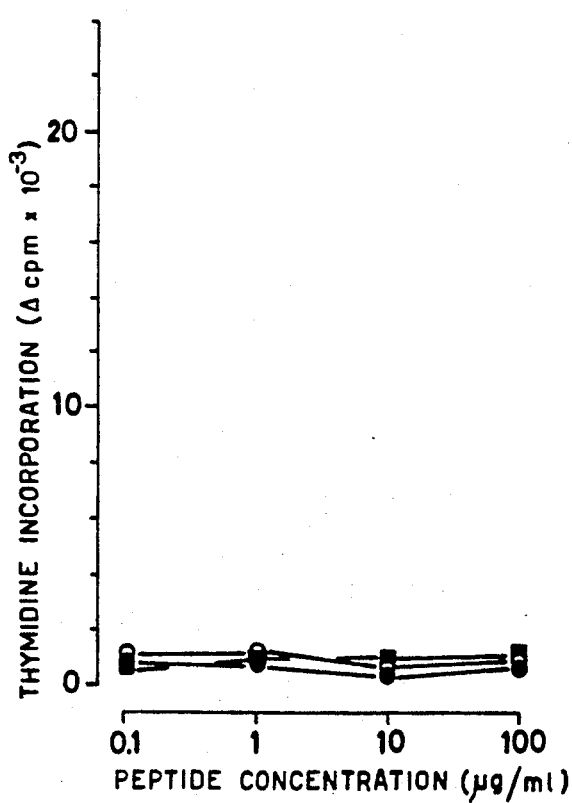

FIGS. 2A and 2B (Cellular proliferation):

The lymphonode cells are collected from C57BL/6 mice (FIG. 2A) and BALB/c mice (FIG. 2B) 10-12 days after the second immunization with RI-(NANP)$_3$-NA.

The results are expressed as the difference in cpm obtained in wells containing different concentrations of RI-(NANP)$_3$-NA (o), (NANP)$_{40}$ (○) and RI (□) and wells containing DMEM.

FIG. 3 (Specificity of anti-(NANP)$_n$ and anti-RI antibodies in C57BL/6 mice immunized by means of RI-(NANP)$_3$-NA peptide).

The sera withdrawn 6 days after the last immunization are mixed with (NANP)$_{40}$ or RI peptides and are tested, in double, by the ELISA test on slabs containing (NANP)$_{40}$ or RI.

The results are compared to those obtained with not competing sera. For comparative purposes, the results are reported which, are obtained with sera of C57BL/6 mice immunized with (NANP)$_{40}$ peptide.

FIG. 4 (Specificity of human anti-RI antibodies).

The sera of suspected malariated persons are mixed with different amounts of (NANP)$_{40}$ or RI (o) peptide and are then submitted to an ELISA test on slabs coated with RI peptide (10 μg/ml). (□): Not competing sera.

The following experimental examples are illustrative and not limitative of the same invention.

EXAMPLE 1

Synthesis of:
Lys-Pro-Lys-His-Lys-Lys-Leu-Lys-Gln-Pro-Gly-Asp-Gly-Asn-Pro-(Asn-Ala-Asn-Pro)$_3$-Asn-Ala-[RI-(NANP)$_3$-NA]

The synthesis of the peptidic conjugate was carried out on an automatic Beckman synthetizer model 990 B, using a commercial polyacrylamidic resin (Cambridge Research Biochemicals) functionalized with norleucine, as the internal reference aminoacid, and p-hydroxymethylphenoxy acid as the reversible peptide-resin connection hook.

One gram of so-functionalized resin was swollen with 32 ml of N,N-dimethylformamide (DMF) for 16 hours at room temperature (20°-25° C.) and was then washed 10 times, 1 minute each time, with DMF.

The first aminoacidic radical (Ala) was then esterified onto the resin, by means of the reaction with the symmetrical anhydride of the aminoacid, protected on its α-amino group with fluorenylmethyloxycarbonyl (Fmoc) protecting group. 2.17 g (1.8 mmol) of (Fmoc-Ala)$_2$O were reacted with the resin in 16 ml of DMF, in the presence of 0.022 g (0.18 mmol) of 4-dimethylaminopyridine (DMAP) and 0.200 ml (1.8 mmol) of N-methylmorpholine (NMM) at room temperature (20°-25° C.) for 30 minutes. At the end of the reaction of esterification, the resin was washed 5 times, each time 1 minute, with DMF; twice, once for 3 minutes and once for 7 minutes, with a (20:80, v/v) piperidine/DMF solution, for the purpose of removing the Fmoc protecting group, and finally 10 times, each time 1 minute, with DMF.

Then, the other aminoacids were all introduced, one at a time, according to the desired sequence, by means of the reaction of acylation between the Fmoc-α-amino protected, activated-carboxy aminoacidic radical, and the growing polypeptidic chain. Between an acylation reaction and the next one, the operations of washing with DMF and of removal of Fmoc group were performed as reported above.

The acylation reaction was carried out at room temperature (20°-25° C.) for 60 minutes. The aminoacidic radicals Lys, Leu, Ala, Pro, Asp and Gly (1.8 mmol of the symmetrical anhydride in 16 ml of DMF) were introduced as symmetrical anhydrides, Asn and Gln were introduced as their p-nitrophenylesters (1.8 mmol) in 16 ml of DMF, in the presence of 0.244 g (1.8 mmol) of 1-hydroxybenzotriazole (HOBT). Finally, Fmoc-His radical was activated in situ by means of the addition of 1.115 g (1.8 mmol) of Fmoc-His (Trt) OH and 0.371 g (1.8 mmol) of dicyclohexylcarbodiimide (DCI) dissolved in 16 ml of DMF, directly in the reactor containing the resin.

The symmetrical anhydride of the protected aminoacids was prepared, immediately before the acylation reaction, by reacting 3.6 mmol of Fmoc-aminoacid with 0.371 g (1.8 mmol) of DCI in 20 ml of CH$_2$Cl$_2$ at room temperature for 10 minutes. At reaction end, dicyclohexylurea was filtered off, the solvent was evaporated and the so-obtained symmetrical anhydride was recovered.

For each acylation reaction, the completion of the formation of the amidic bond was verified by means of the ninhydrin test (E. Kaiser et al., Anal. Biochem. 34, 595, 1980) and the trinitrobenzenesulphonic acid test (W. S. Hancock et al., Anal. Biochem., 71 261, 1976). The samples were drawn after 30 minutes of reaction, and gave positive results.

At the end of the assemblage of the desired sequence, the aminoacidic analysis of the peptide-resin was performed, with the following results being obtained:

| His | Leu | Lys | Glx | Gly | Asx | Pro | Ala | Nle |
|---|---|---|---|---|---|---|---|---|
| 0.88 | 1.00 | 5.04 | 1.11 | 2.19 | 9.11 | 5.89 | 4.61 | 1.25 |

The theoretical values for the same aminoacids are respectively:

| His | Leu | Lys | Glx | Gly | Asx | Pro | Ala |
|---|---|---|---|---|---|---|---|
| 1.00 | 1.00 | 5.00 | 1.00 | 2.00 | 9.00 | 6.00 | 4.00 |

By Glx: either Gln or Glu is meant.
By Asx: either Asn or Asp is meant.

The so-synthetized peptide was then removed from the resin by means of the reaction with 50 ml of (90:10 v/v) trifluoroacetic acid/water solution at a temperature of 20° C. for 3 hours. The resin was then separated from the reaction mixture by filtration under vacuum, washed 3 times, each time with 20 ml of water, and filtered. The filtrates were combined and were concentrated to dryness by evaporation, they were then dissolved again in water and freeze-dried.

The so-obtained polypeptide (1.255 g, 0.405 mmol) was purified by gel-filtration chromatography, using a column of 84×2.6 cm, a fine Sephadex G-25 resin and 0.1 M CH$_3$COOH as the eluent.

The peptide was furthermore purified by ion-exchange chromatography, using a column of 45×2.0 cm, a Whatmann CM-52 resin and eluting with a gradient of ammonium acetate from 0.1M to 0.5M, pH 6.6. The fractions corresponding to the purified peptide were collected and freeze-dried.

The total chromatographic purity resulted of 74%. The purified fraction corresponds to 40% of the peptide removed from the resin. The analysis of the purified peptide for its aminoacidic content, as determined by hydrolysis with 6N HCl at 110° C. for 20 hours, is as follows:

| His | Leu | Lys | Glx | Gly | Asx | Pro | Ala |
|-----|-----|-----|-----|-----|-----|-----|-----|
| 1.00 | 1.00 | 4.78 | 1.08 | 1.99 | 8.75 | 6.18 | 3.99 |

Theoretical values:

| His | Leu | Lys | Glx | Gly | Asx | Pro | Ala |
|-----|-----|-----|-----|-----|-----|-----|-----|
| 1.00 | 1.00 | 5.00 | 1.00 | 2.00 | 9.00 | 6.00 | 4.00 |

EXAMPLE 2

Immunogenicity of RI-(NANP)$_3$-NA Polypeptide 8-12 weeks old C57BL/6 (ISREC, Lausanne, Switzerland), C57BL/10, B10.A (5R), BALB/c and CBA/Ca (CMU, Geneva, Switzerland) mice, of both sexes, were immunized with RI-(NANP)$_3$-NA polypeptide and with the peptide corresponding to region I only (RI), with both of them being synthetized as disclosed in Example 1.

In particular, the peptides were dissolved in water at a concentration of 10 μg/ml, emulsified at a 1:1 rate with complete Freund's adjuvant (DIFCO Laboratories, Detroit, Mich.) and 50 μl of said emulsions were inoculated into the basis of the mice tail, by intramuscular way.

The inoculation was repeated 15 days later, by using incomplete Freund's adjuvant, and still 15 days later by inoculating, by intraperitoneal way, 500 μl/mouse of saline solution containing RI and RI-(NANP)$_3$-NA peptides.

Then, blood withdrawals from retroocular plexus were carried out on different days, and up to 6 days after the last inoculation.

The individual sera were then analyzed for determining the presence therein of specific anti-Region I antibodies, by means of the ELISA method, using slabs coated with 10 μg/ml of RI peptide and 1 μg/ml of (NANP)$_{40}$ peptide as disclosed in U.S. Pat. application filed on Apr. 10, 1986 under number 850135.

The results, reported in FIG. 1A, show the absence of anti-RI antibodies in the sera of mice immunized by means of RI peptide only, and the presence, 17 days later than the first inoculation, of anti-(NANP) antibodies in C57BL/6 mice immunized with RI-(NANP)$_3$-NA polypeptide.

The amount of said antibodies increases after the second and third inoculation because of the appearance of anti-RI antibodies (FIG. 1B).

The presence of specific anti-Region I antibodies was determined, by means of the ELISA test, in the sera (93) of persons living in regions wherein malaria is endemic (Gabon) and in the sera (102) of healthy persons.

As it can be observed from following Table 1, anti-RI antibodies were detected in 39 sera. 34% of these result positive also for anti-(NANP)$_{40}$ antibodies, whilst 5 sera result positive for anti-RI antibodies only.

TABLE 1

Frequency of Anti-(Asn—Ala—Asn—Pro)$_{40}$ ((NANP)$_{40}$) and Anti-Region I (RI) Antibodies in the Sera of Persons From Gabon

|  |  | Anti-(Asn—Ala—Asn—Pro) Antibodies | | |
|---|---|---|---|---|
|  |  | Positive | Negative | Total |
| Anti-(RI) | Positive | 34 (36.5) | 5 (5.3) | 39 (41.8) |
| Antibodies | Negative | 27 (29.1) | 27 (29.1) | 54 (58.2) |
|  | Total | 61 (65.6) | 32 (34.4) |  |

The sera were considered as positive when their OD value at 492 nm was higher than 0.25, when computed as the average value of the OD values obtained by testing 102 sera (diluted to 1:200) of healthy persons.

The specificity of anti-RI antibodies and anti-(NANP) antibodies was determined on the serum of C57BL/6 mice respectively immunized with (NANP)$_{40}$ peptide and RI-(NANP)$_3$-NA polypeptide.

The sera, withdrawn 6 days after the last inoculation, were diluted to 1:200 and were mixed with (NANP)$_{40}$ and RI peptides (250 μg/ml) in PBS containing 0.05% of Tween 20, and 2.5% of milk powder and were then incubated at 37° C. for 1 hour.

One hundred μl of said mixtures were tested, in double run, by the ELISA test, using slabs coated with (NANP)$_{40}$ peptide and RI peptide.

The results, reported in FIG. 3, show that only the analogous peptides inhibit the bond between the antibodies and the peptides adsorbed on the slabs.

Furthermore, FIG. 4 shows that the bond between the antibodies present in the positive sera of persons exposed to malarial infection and RI peptide is inhibited when all of the sera are pre-incubated with RI.

EXAMPLE 3

Cellular Proliferation Induced by RI-(NANP)$_3$-NA Polypeptide

The inguinal and periaortic lymphonodes of the mice immunized as shown in Example 1, were collected 8-10 days after the second inoculation. The cells were suspended in DMEM containing L-glutamine (2 mM), HEPES buffer (25 mM), 2-mercaptoethanol (5×10$^5$) and foetal seroalbumin (5%) and then seeded (2×10$^5$) in 200 ml of culture medium in microslabs (Greiner, Nurtingen, Federal Republic of Germany) in the presence of 0.1; 1.0; 10.0 and 100 μg/ml of the peptides to be tested.

Four days later, the cultures were irradiated with 1 μCi of [$^3$H]-thymidine and, 18 hours later, the cells were collected and the therein incorporated thymidine was measured.

The results, reported in FIG. 2A, show a high cellular proliferation for C57BL/6, C57BL/10 and B10.A (5R) mice, in the presence of 10 μg/ml of RI-(NANP)$_3$-NA peptide and of (NANP)$_4$ peptide, and the absence of a cellular proliferation in all of mice immunized with the RI peptide.

These results show that the (NANP)$_3$ peptide linked to the region I acts as an immunogen carrier, and stimulates the epitope RI-specific antibody response.

EXAMPLE 4

Test of Inhibition of RI-$(NANP)_3$-NA on the Penetration of the Sporozoites into Human Hepatocytes Human hepatoma cells were seeded at a concentration of $10^5$ cells/chamber in Lab.-Tek plastic chambers (Miles) and cultivated for 24–48 hours Then, to each chamber 25 μl was charged of a suspension containing 5-$10^4$ sporozoites of *P. falciparum* and 25 μl of a 1:5 solution of the sample under test.

The sporozoites were obtained from salivary glands of *Anopheles stephensi* infected with *P. falciparum.*

Two and six days later, the number of infected hepatocytes was determined by immunofluorescence by using monoclonal anti-*P. falciparum* CS protein antibodies.

The results obtained show that the sera of C57BL/6 mice immunized with RI-$(NANP)_3$-NA inhibit (86%) the penetration of the sporozoites of *P. falciparum* into the hepatic cells, and that said inhibition is higher than that obtained with the sera of mice immunized with peptide $(NANP)_{40}$ only.

We claim:

1. A polypeptide useful for the preparation of antimalarial vaccines and of diagnostic kits for the detection of antisporozoite antibodies in clinical samples, which consists essentially of a synthetic peptide repeating Region I of the circumsporozoitic protein of *Plasmodium falciparum* and units of a repeating tetrapeptide of the circumsporozoitic protein of *Plasmodium falciparum*, linked by an amidic bond between the tail proline of n I of the peptide and the head asparagine of the first tetrapeptide of the repeating tetrapeptide units, the polypeptide having the formula: Lys-Pro-Lys-His-Lys-Lys-Leu-Lys-Gln-Pro-Gly-Asp-Gly-Asn-Pro-(Asn-Ala-Asn-Pro)$_n$-Asn-Ala wherein n is from 3 to 40.

2. The polypeptide according to claim 1, wherein n is from 3 to 10.

* * * * *